(12) United States Patent
Kettlewell et al.

(10) Patent No.: US 9,884,137 B2
(45) Date of Patent: Feb. 6, 2018

(54) ABSORBENT MATERIALS

(71) Applicant: Speciality Fibres and Materials Limited, London (GB)

(72) Inventors: Graeme Kettlewell, Coventry (GB); Phillip Baker, Coventry (GB)

(73) Assignee: Speciality Fibres and Materials Limited, London (GB)

( * ) Notice: Subject to any disclaimer, the term of this patent is extended or adjusted under 35 U.S.C. 154(b) by 43 days.

(21) Appl. No.: 14/433,622

(22) PCT Filed: Sep. 30, 2013

(86) PCT No.: PCT/GB2013/052539
§ 371 (c)(1),
(2) Date: Apr. 3, 2015

(87) PCT Pub. No.: WO2014/053815
PCT Pub. Date: Apr. 10, 2014

(65) Prior Publication Data
US 2015/0250919 A1    Sep. 10, 2015

(30) Foreign Application Priority Data

Oct. 5, 2012 (GB) .................................. 1217872.9

(51) Int. Cl.
| | | |
|---|---|---|
| *A61L 15/60* | (2006.01) | |
| *A61F 13/00* | (2006.01) | |
| *A61L 15/22* | (2006.01) | |
| *D01F 6/16* | (2006.01) | |
| *D01G 13/00* | (2006.01) | |

(52) U.S. Cl.
CPC ........ *A61L 15/60* (2013.01); *A61F 13/00987* (2013.01); *A61L 15/225* (2013.01); *D01F 6/16* (2013.01); *D01G 13/00* (2013.01)

(58) Field of Classification Search
CPC .......... A61F 13/00012; A61F 13/00017; A61F 13/15617; A61F 2013/530481; A61F 2013/530489; A61F 2013/5307; A61F 2013/15943; A61F 2013/530605; A61F 2013/53062; A61L 15/22; A61L 15/225; A61L 15/28; A61L 15/60
See application file for complete search history.

(56) References Cited

U.S. PATENT DOCUMENTS

| 5,582,786 | A  | 12/1996 | Brunskill et al. |
| 6,471,982 | B1 | 10/2002 | Lydon et al. |
| 7,229,689 | B2 | 6/2007  | Qin et al. |
| 7,820,873 | B2 | 10/2010 | Sun et al. |
| 8,921,427 | B2 | 12/2014 | Rohrer et al. |
| 9,144,625 | B2 | 9/2015  | Law et al. |
| 9,221,963 | B2 | 12/2015 | Law |
| 2001/0041876 | A1* | 11/2001 | Creagan ............ A61F 13/15203 604/368 |
| 2003/0139714 | A1 | 7/2003 | Sun et al. |
| 2005/0101900 | A1 | 5/2005 | Qin et al. |
| 2006/0014006 | A1 | 1/2006 | Hermeling et al. |
| 2009/0306157 | A1 | 12/2009 | Rohrer et al. |
| 2010/0129633 | A1 | 5/2010 | Law |
| 2010/0262090 | A1* | 10/2010 | Riesinger .......... A61F 13/00017 604/304 |
| 2011/0004172 | A1 | 1/2011 | Eckstein et al. |
| 2011/0238025 | A1 | 9/2011 | Law |
| 2013/0288556 | A1* | 10/2013 | Moore .................. D04H 1/435 442/334 |
| 2014/0249495 | A1* | 9/2014 | Mumby ............ A61F 13/00059 604/359 |
| 2016/0114074 | A1 | 4/2016 | Law |

FOREIGN PATENT DOCUMENTS

| CN | 1450918 | 10/2003 |
| CN | 1708355 | 12/2005 |
| CN | 1799640 | 7/2006 |
| CN | 101360519 | 2/2009 |
| CN | 102292112 | 12/2011 |
| CN | 102580137 | 7/2012 |
| CN | 1684719 A | 10/2015 |
| CN | 2013800522170 | 3/2016 |
| CN | 2013800522170 | 4/2017 |
| CN | 2013800522170 | 8/2017 |
| DE | 20118880 | 1/2002 |
| DE | 10-2007-049430 A1 | 4/2009 |
| DE | 102007063294 | 7/2009 |
| DE | 20118880 | 7/2015 |
| EP | 1435247 | 7/2004 |
| GB | 2270030 | 3/1994 |
| GB | 1217872.9 | 2/2013 |
| WO | WO 02/36866 | 5/2002 |
| WO | WO PCT/GB2013/052539 | 2/2014 |
| WO | WO PCT/GB2013/052539 | 4/2015 |

* cited by examiner

*Primary Examiner* — Lynne Anderson
(74) *Attorney, Agent, or Firm* — Wells St. John P.S.

(57) ABSTRACT

Provided is an absorbent material and a method of making an absorbent material. The absorbent material comprises a blend of a super-absorbent first type of gel-forming fiber with a second type of gel-forming fiber, wherein the super-absorbent first type of gel-forming fiber is formed from a super-absorbent polymer. Such absorbent materials are useful in the manufacture of absorbent articles such as wound dressings.

16 Claims, No Drawings

ABSORBENT MATERIALS

CROSS REFERENCE TO RELATED APPLICATION

This application is a 35 U.S.C. § 371 of and claims priority to PCT International Application No. PCT/GB2013/052539 which was filed on 30 Sep., 2013, and was published in English, and claims priority to GB Patent Application No. 1217872.9, which was filed on 5 Oct., 2012, the teachings of which are incorporated herein by reference.

The present invention relates to absorbent materials useful in the manufacture of absorbent articles such as wound dressings, and in particular wound dressings for the treatment of chronic, non-healing wounds.

Absorbent fibres useful as components in advanced wound care dressings are known in the art, particularly fibres based on alginic acid, carboxymethylcellulose (CMC), carboxymethylchitosan, cellulose ethyl sulfonate (CES) and salts thereof.

Alginate fibres have been known for some time as being useful in the preparation of surgical dressings. For example, United Kingdom Patent No. 653341 (Bonniksen), published in 1951, describes surgical dressings formed from fibres of calcium alginate. Even then, however, it was known that a failing of calcium alginate fibres is their relative insolubility and lack of absorbency in water or wound exudate matter. Bonniksen in GB653341 therefore proposed that a proportion of the calcium ions in calcium alginate be replaced by sodium cations, since sodium alginate was known to be more soluble than calcium alginate. The resulting process has become known as "conversion" of calcium alginate to form a mixed salt alginate.

Dressings based on fibres of alginic acid or its salts have moderate overall absorbency of wound fluid, but suffer from slow absorption due to the need to exchange multivalent ions binding the fibrous structure together with sodium ions present in wound fluid. Although this ion exchange renders the fibres swellable in ion containing aqueous media, allowing absorption of fluid, the mechanical strength of the gelled fibres is compromised, and it is not routinely possible to remove a saturated dressing in one piece. Frequently, the dressing must be irrigated with saline to wash it away, and this can be traumatic for the patient.

Fibrous wound dressings with a weight for weight absorbency higher than that of calcium alginate are known. For example, the commercial dressing AQUACEL (®) (sold by ConvaTec Inc of Skillman, New jersey, USA) is based on a blend of chemically modified cellulose and alginate fibres. The commercial dressing DURAFIBER (®) (sold by Smith and Nephew of Hull, United Kingdom) is made from a blend of cellulose fibres (TENCEL) and CES fibres. Both AQUACEL (®) and DURAFIBER (®) have a stated absorbency in 0.9% saline of greater than 20 g/100 $cm^2$ or 18 g/g. However, both are more expensive than calcium alginate dressings.

The use of polyacrylates as absorbent materials is known in the art. Polyacrylate absorbent materials are typically provided as a powdered format which may be contained within a bag-like material. In fibrous form polyacrylates may be blended with thermoplastic bicomponent fibres to improve physical strength. This combination will be passed through a calendar or an oven at a high temperature sufficient to cause the thermoplastic bicomponent fibres to fuse creating a cross-linked network that provides strength. This a costly and time consuming process with significant expenditure on equipment. Furthermore the required airlaid equipment used to produce the fabric does not lend itself well to medical device manufacture, is typically large in scale, and often not located in a suitable clean environment.

Multi-layered wound dressings are known. Such dressings may comprise an alginate wound-contact layer and a multi-laminar backing layer. The backing layer may comprise an outer layer or backing formed from a blend of fluff pulp and low melt binder, and a core absorbency layer which may be a blend of fluff pulp, gel-forming polymer fibres and low melt binder. Although these dressings have high absorbency, due to their multiple layers they are typically very thick and inflexible, having a typical weight of 250-300 $g/m^2$.

Where a wound is exuding heavily, the properties of an ideal dressing are good integrity, high absorbency and low lateral wicking. Good integrity ensures that the dressing is easy to handle. High absorbency means that an efficient uptake of exudate, together with its associated toxins and other undesirable matter, can be achieved. Low lateral wicking may help to prevent maceration of the periwound area.

In addition to damaging the wound, exudate damages the periwound tissue exposed to it as well. In particular, exudate that flows out of the wound and onto the periwound region may damage the fragile skin, which is already compromised due to the patients underlying etiology, such as diabetes. Such damage may degrade the periwound skin and cause its breakdown and turn it into a wound. Thus, exudate flow onto the periwound region will cause many complications, including, the potential for increasing the size of the wound and prolonging its healing. Such damage to the skin in the periwound region (periwound skin) makes it more susceptible to tearing and resultant intense pain as dressings or devices adhered to them are removed. Other complications include infection of the periwound region and intense itching.

It is an object of the present invention to mitigate at least some of the problems described above.

According to a first aspect of the present invention there is provided an absorbent material comprising a blend of a super-absorbent first type of gel-forming fibre with a second type of gel-forming fibre, wherein the super-absorbent first type of gel-forming fibre is formed from a super-absorbent polymer.

By the term 'blend' it will be appreciated that the super-absorbent first type of gel-forming fibres and the second type of gel-forming fibres are intimately mixed so as to form a homogenous mixture of fibres. The first and second types of gel forming fibres are thus evenly distributed throughout the material.

It will be understood that a super-absorbent polymer is a polymer which is capable of absorbing water in an amount as much as 500 times its own weight. In some embodiments, the super-absorbent polymer is capable of absorbing at least 15, at least 20, at least 30, at least 50, at least 75 or at least 100 g of liquid per g of fibre.

In some embodiments, the super-absorbent polymer is not modified cellulose.

In some embodiments, the super-absorbent polymer is selected from the group consisting of: polyacrylates or co-polymers thereof; polymers of anhydrides, such as poly (maleic anhydride), or co-polymers thereof; polymers with carboxylic acid groups or salts thereof, such as polymers of acrylic acid, maleic acid, methacrylic acid or derivatives thereof; polymers of acrylamide (e.g. polyacrylamide) or co-polymers thereof; polyethylene oxide (PEO); polyvinyl alcohol (PVOH); graft co-polymers; or mixtures thereof.

In some embodiments, the super-absorbent polymer is a polyacrylate or copolymer thereof. Polyacrylates are a broad group of synthetic polymers derived from monomers which include esters of acrylic acid, for example poly(hydroxyl methacrylate), and salts of polymers of acrylic acid and derivatives thereof.

Suitable polyacrylates or copolymers thereof for use in the invention include sodium polyacrylate, sodium polymethacrylate, and co-polymers of acrylic acid with other monomers. Examples include co-polymers of acrylic acid with vinyl pyrrolidone monomers, optionally with a diacrylate cross-linker, co-polymers of acrylic acid with maleic acid or hydrolysed maleic anhydride. Co-polymers may also comprise olefins, such as ethylene.

In some embodiments the polymers or co-polymers are cross-linked.

One example of polyacrylate fibres is 'SAF' (™), commercially available fibres sold by Technical Absorbent Limited (Grimsby, UK). SAF (™) is formed from a cross-linked polymer of acrylic acid (AA) methylacrylate (MA) and a small quantity of special acrylate/methylacrylate monomer (SAMM) in which the acrylic acid is partially neutralised to the sodium salt of acrylic acid (AANa). SAF (™) fibres are available in different staple lengths, linear density and with different degrees of cross linking to give different absorbency levels.

Suitable polymers of acrylamide or copolymers thereof include polyacrylamide, polyAMPs (poly-acrylamido-2-methylpropane sulfonic acid) or its sodium salt, and acrylamide-co-acrylic acid.

Graft polymers are polymers grafted onto a polysaccharide backbone. The graft polymer may be a homopolymer or a copolymer. Suitable polymers for the formation of graft polymers include polyacrylic acid or acrylamide-co-acrylic acid. The polymers may be grafted on to chitosan, cellulose, starch, guar gum, carrageenan, alginate, or synthetic polymers such as PVOH.

The second type of gel forming fibre may be a polysaccharide. Suitable polysaccharides include alginate (i.e. a salt of alginic acid), modified cellulose, modified chitosan, guar gum, carrageenan, pectin, starch or mixtures thereof. The term 'modified' will be understood as meaning that the polysaccharide molecules have been chemically modified, for example by covalent attachment of additional functional groups. Examples of modified cellulose include carboxymethylcellulose (CMC), cellulose ethyl sulfonate (CES) and cellulose ethyl sulfonate. Examples of modified chitosan include carboxymethylchitosan, ethyl sulfonated chitosan and carboxyethyl chitosan.

In some embodiments, the second type of gel forming fibre is not formed from modified cellulose. In some embodiments, neither of the first or second types of gel-forming fibres is formed from modified cellulose.

The alginate salt may comprise a monovalent cation or a multivalent cation, in particular a divalent cation provided that the divalent cation is not $Mg^{2+}$. In some embodiments, the alginate is calcium alginate, sodium calcium alginate, sodium alginate, silver alginate, copper alginate or mixtures thereof. In some embodiments, the alginate is calcium alginate.

Alginate fibres with a range of M/G ratios (the ratio of D-mannuronate to L-guluronate) may be used. The M:G ratio may be from 0:100 to 100:0. The amount of M relative to the total amount of M plus G may be at least 20, at least 30, at least 40, at least 50, at least 60, at least 70%. The amount of M relative to the total amount of M plus G may be no more than 80%, no more than 70%, no more than 60%, no more than 50% or no more than 40%. The amount of G relative to the total amount of M plus G may be at least 20, at least 30, at least 40, at least 50, at least 60, at least 70%. The amount of G relative to the total amount of M plus G may be no more than 80%, no more than 70%, no more than 60%, no more than 50% or no more than 40%.

The combination of fibres made from super-absorbent polymer and alginate fibres is thought to be particularly advantageous because the two different fibres provide different rates of absorption of liquids. This is particularly beneficial for absorption of wound exudates. The alginate fibres will tend to favour the absorption of a high salt exudate, while the super-absorbent polymer fibres will have a higher absorption rate for low salt exudate.

In some embodiments, the super-absorbent polymer is a polyacrylate and the second type of gel-forming fibre is alginate.

In some embodiments, the absorbent material comprises at least 5%, at least 10%, at least 20%, at least 30%, at least 40% or at least 50% of the super-absorbent first type of gel-forming fibres, by weight of the total fibre content of the material. In some embodiments, the absorbent material comprises no more than 60%, no more than 50%, no more than 40%, no more than 30% or no more than 20% of the super-absorbent first type of gel-forming fibres. In some embodiments, the absorbent material comprises from 10 to 30% of the super-absorbent first type of gel-forming fibres, by weight of the total fibre content of the material.

In some embodiments, the absorbent material comprises at least 30%, at least 40%, at least 50%, at least 60%, at least 70% or at least 80% of the second type of gel forming fibres, by weight of the total fibre content of the material. In some embodiments, the absorbent material comprises no more than 90%, no more than 80%, no more than 70%, no more than 50% or no more than 40% of the second type of gel forming fibres. In some embodiments, the absorbent material comprises from 50 to 70% of the second type of gel forming fibres, by weight of the total fibre content of the material.

In some embodiments, the absorbent material additionally comprises reinforcing fibres. Reinforcing fibres are added to increase the strength of the absorbent material, particularly when wet. Reinforcing fibres are described in Hansen, U.S. Pat. No. 5,981,410 titled "Cellulose-Binding Fibres"; Stengaard et al., U.S. Pat. No. 6,811,716 titled "Polyolefin Fibres and Method for the Production Thereof"; Jensen et al., U.S. Pat. No. 5,958,806 titled "Cardable Hydrophobic Polyolefin Fibres Comprising Cationic Spin Finishes;" all of which are incorporated by reference.

In some embodiments, the reinforcing fibres are thermoplastic bicomponent fibres. The thermoplastic bicomponent fibres may have a polyolefin component. Thus, the thermoplastic bicomponent fibres may comprise a polyolefin-containing polymeric material of which the largest part (by weight) consists of homo- or copolymers of monoolefins such as ethylene, propylene, 1-butene, 4-methyl-1-pentene, etc. Examples of such polymers are isotactic or syndiotactic polypropylene, polyethylenes of different densities, such as high density polyethylene, low density polyethylene, and linear low density polyethylene and blends of the same. The polymeric material may be mixed with other non-polyolefin polymers such as polyamide or polyester, provided that polyolefins still constitute the largest part of the composition. The melts used to produce the polyolefin-containing fibres may also contain various conventional fibre additives, such as calcium stearate, antioxidants, process stabilizers, compatibilizers, and pigments. Methods for applying the thermoplastic bicomponent fibres are described in EP0740554; EP0171806; Ejima et al., U.S. Pat. No. 5,456,982; Davies, U.S. Pat. No. 4,189,338; Davies, U.S. Pat. No. 3,511,747; and Reitboeck et al., U.S. Pat. No. 3,597,731, all of which are incorporated herein by reference.

The thermoplastic bicomponent fibres may be of the sheath-core type with the core being located either eccentrically (off-centre) or concentrically (substantially in the centre), or of the side-by-side type, in which each of the two components typically has a semi-circle cross section. Bicomponent fibres having irregular fibre profiles are also contemplated, e.g., an oval, ellipse, delta, star, multilobal, or other irregular cross section, as well as splittable fibres.

The thermoplastic bicomponent fibres will typically have a high melting and low melting polyolefin component which comprise, respectively, polypropylene/polyethylene (the polyethylene comprising HDPE, LDPE, and/or LLDPE), high density polyethylene/linear low density polyethylene, polypropylene random copolymer/polyethylene, or polypropylene/polypropylene random copolymer.

Preferred thermoplastic bicomponent fibres are commercially available from Fiber Visions, Inc (Athens, Ga., USA). The thermoplastic bicomponent fibres may have a linear density of from 1.5 to 17 decitex.

In some embodiments, the reinforcing fibres are cellulose fibres. The cellulose fibres may be formed from modified cellulose or non modified cellulose. In some embodiments, the reinforcing fibres are lyocell fibres, which are made from solvent spun cellulose. These may be obtained by an organic solvent spinning process, for example using various amine oxides as solvents. In particular, N-methylmorpholine-N-oxide ("NMNO") with water (about 12%) proves to be a particularly useful solvent.

Examples of processes for preparing cellulose fibres are described in McCorsley et al., U.S. Pat. Nos. 4,142,913; 4,144,080; 4,211,574; 4,246,221; and 4,416,698, and others. Jurkovic et al., U.S. Pat. No. 5,252,284 and Michels et al., U.S. Pat. No. 5,417,909 deal especially with the geometry of extrusion nozzles for spinning cellulose dissolved in NMMO. Brandner et al., U.S. Pat. No. 4,426,228 is exemplary of a considerable number of patents that disclose the use of various compounds to act as stabilizers in order to prevent cellulose and/or solvent degradation in the heated NMMO solution. Franks et al., U.S. Pat. Nos. 4,145,532 and 4,196,282, deal with the difficulties of dissolving cellulose in amine oxide solvents and of achieving higher concentrations of cellulose. All of these patents are incorporated herein by reference. Lyocell fibres are commercially available under the brand name TENCEL (®) from Lenzing AG, Austria.

Other types of reinforcing fibres may be made from polyester, polyethylene, polypropylene or polyamide.

In some embodiments, the reinforcing fibres are not formed from modified cellulose.

In some embodiments, the absorbent material comprises at least 5%, at least 10%, at least 15%, at least 20% or at least 25% reinforcing fibres. In some embodiments, the absorbent material comprises no more than 30%, no more than 25% or no more than 20% reinforcing fibres.

In some embodiments the reinforcing fibres have a linear density of from 0.1 to 15 decitex, from 0.3 to 12 or from 0.5 to 10 decitex. In some further embodiments, the reinforcing fibres have a linear density of from 0.7 to 5.0, from 0.8 to 2.5, from 0.9 to 2.0 or from 1.2 to 1.6 decitex. It has been surprisingly found that when low density fibres (i.e., fibres having a density of less than 2.0 decitex) are incorporated into the composite absorbent article the wet strength is improved while absorbency is not compromised.

In some embodiments, the absorbent material comprises from 10 to 30% of the super-absorbent first type of gel-forming fibres, from 50 to 70% of the second type of gel-forming fibres, and from 10 to 20% reinforcing fibres, by weight of the total fibre content of the material. In a particular embodiment, the absorbent material comprises 20% of the super-absorbent first type of gel-forming fibres, 60% of the second type of gel-forming fibres and 20% reinforcing fibres, by weight of the total fibre content of the material.

In further embodiments, the absorbent material comprises from 50 to 70% alginate, from 10 to 30% polyacrylate and from 10 to 20% reinforcing fibre. The absorbent material may comprise 60% alginate, 20% polyacrylate and 20% reinforcing fibre (e.g. TENCEL), by weight of the total fibre content of the material. The absorbent material may comprise 50% alginate, 30% polyacrylate and 20% reinforcing fibre, by weight of the total fibre content of the material.

The fibres (i.e. the super-absorbent first type of gel-forming fibres, the second type of gel-forming fibres and, optionally, the reinforcing fibres) may constitute at least 70%, at least 80%, at least 85%, at least 90%, at least 95%, at least 97%, at least 98% or at least 99% by weight of the total absorbent material. In some embodiments, the fibres constitute 100% of the material.

In some embodiments, the absorbent material has a weight of from 100 to 150, from 110 to 140 or from 120 to 130 g/m2.

In some embodiments, the absorbent material has an absorbency of more than 16, more than 17, more than 18, more than 19, more than 20, more than 22 or more than 25 grams of liquid per gram of material.

In some embodiments, the absorbent material has a tensile strength (cross direction), as measured by the method described in Example 2, of at least 1 N/cm.

The absorbent material of the invention may be in sheet form. In some embodiments, the material is non-woven. The material may be made by carding, air-laying and/or needle-punching the fibres, or by or hydro-entangling the fibres using a non-aqueous solvent. In some embodiments, the absorbent material is made by a method comprising carding and, optionally, needle bonding the fibres. In some embodiments wherein the material comprises a biocomponent thermoplastic reinforcing fibre, the material is made by the air-laying or carding followed by heating to fuse the bicomponent thermoplastic filaments. It has been previously perceived that super-absorbent fibres cannot be processed using methods such as carding and needle bonding because they are too brittle. Difficulties in fibre opening and web forming during processing of high absorbency fibres into non-woven material are also known. However, the inventors have surprisingly found that super-absorbent gel-forming fibres, such as polyacrylates, are suitable for processing using these methods.

Methods for including reinforcing fibres into nonwoven structures are well known from, for example, GB1207352, which is also incorporated by reference.

The absorbent material may comprise one or more optional ingredients such as preservatives, antimicrobial agents or other pharmacologically active agents. For example, antibiotics (e.g. penicillin), antimicrobial agents (such as silver, PHMB (polyhexamethylene biguanide)), antiseptic agents (e.g. povidone iodine), anti-inflammatory agents (such as hydrocortisone), or other agents (such as zinc oxide) may be included. Such optional agents may be applied to the absorbent material or article by spraying, coating, dipping or by any other method known to those skilled in the art.

According to a second aspect of the present invention there is provided an absorbent article comprising the absorbent material according to the first aspect of the invention.

The absorbent articles may include wound dressings, disposable sanitary articles such as nappies (diapers), disposable nappies and training pants, feminine care products, e.g., tampons, sanitary towels, or napkins and pant liners, and incontinence products.

The absorbent properties and biodegradability of the absorbent material of the invention means that the articles comprising the absorbent material are particularly desirable for use in the personal care sector.

In some embodiments, the absorbent material forms a surface or a part of a surface of the absorbent article which, in use, comes into contact with the skin. In some embodiments, the absorbent article is a wound dressing. The wound dressing may comprise a wound-contacting surface. The wound contacting surface, or a part thereof, may be formed of an absorbent material comprising or consisting of a first type of gel-forming fibre with a second type of gel-forming fibre, wherein the first type of gel-forming fibre is a super-absorbent fibre.

It was previously thought that polyacrylates were not suitable for use in contact with the skin due to toxicity. However, it has now been found that this is not the case. The incorporation of polyacrylates in the wound contact layer is advantageous since polyacrylates thought to aid binding of matrix metalloproteases (MMPs) which are known to delay the healing process. Furthermore, polyacrylates have also been shown to have antimicrobial properties, making them particularly suitable for use in the wound-contact layer of dressings.

The wound dressing may be in the form of swabs, wound pads, wadding ribbons, sponges, nets and bandages. The absorbent material of the first aspect of the invention may form one of a plurality of layers. The wound dressing may further comprise a perforated film which is applied to one or more surfaces of the dressing.

According to a third aspect of the invention there is provided a method for preparing an absorbent material, the method comprising carding a superabsorbent first type of gel-forming fibres, wherein the super-absorbent first type of gel-forming fibres are formed from a super-absorbent polymer. In some embodiments, the super-absorbent first type of gel-forming fibres are blended or mixed with a second type of gel-forming fibres and/or reinforcing fibres prior to carding.

In some embodiments the method is for preparing an absorbent material in accordance with any one of claims 1 to 20. In some embodiments, the super-absorbent polymer is a polyacrylate or a copolymer thereof.

It will be understood that all embodiments described above in relation to the first aspect of the invention may equally apply to the second and third aspects of the invention.

Embodiments of the present invention will now be described by way of example only.

EXAMPLES

Example 1

Calcium alginate fibres were cut to approximately 50 mm length and mixed with polyacrylate fibres ('SAF', purchased from Technical Absorbents Limited, Grimsby, UK) and/or a solvent spun cellulose fibre (TENCEL (®), Lenzing Fibres AG) in the ratios presented in Table 1. The fibres were passed through a sample card and the resultant web was needle bonded. Comparative calcium alginate fabric containing no polyacrylate fibres was manufactured in a similar manner. The absorbency was measured by weighing a 5 cm×5 cm piece of sample material ($W_1$). Next, the sample was placed in Solution A at 37° C. for 30 minutes in a petri dish. Then, the square was lifted out of the petri-dish by holding the square by one corner, and the sample was allowed to drain for 30 seconds. The sample was then reweighed to obtain the end weight ($W_2$). The fabric absorbency is given by $((W_2-W_1)/W_1)$.

TABLE 1

| % (w/w) | | | Absorbency (g/g) | |
|---|---|---|---|---|
| Alginate | TENCEL (RTM) | polyacrylate | Free swell | Retention |
| 100 | 0 | 0 | 16 | 9 |
| 90 | 0 | 10 | 19 | — |
| 80 | 0 | 20 | 19 | 11 |
| 70 | 10 | 20 | 19 | 12 |
| 70 | 0 | 30 | 24 | 14 |
| 60 | 0 | 40 | 27 | 17 |
| 50 | 0 | 50 | 29 | 18 |
| Commercial products | | | | |
| Sorbsan (Calcium alginate) | | | 17 | — |
| AQUACEL (RTM) | | | 16 | — |
| DURAFIBER (RTM) | | | 18 | — |

In the absence of polyacrylate, the absorbency (free swell) of the material was less than that of the commercial products. The inclusion of at least 10% polyacrylate allowed the material to absorb at least as much solution as the commercial products.

Example 2

The lateral wicking of the material was determined by laying a 15 mm×100 mm strip of fabric in a petri dish and subsequently adding 1 g of a saline solution coloured with a blue dye to the centre of the strip using a dropping pipette. The spread of the blue dyed area at the widest point was measured. This was performed in triplicate.

| Mean lateral wicking (mm) | |
|---|---|
| % polyacrylate 20 | 3.3 |
| % polyacrylate 30 | 2.3 |
| DURAFIBER (RTM) | 2.5 |
| AQUACEL (RTM) | 2.4 |

Surprisingly, it was found that material comprising 20% polyacrylate had a mean lateral wicking which was significantly improved over that of the commercial products. Increasing the amount of polyacrylate to 30% resulted in a lateral wicking value which was substantially the same as that of the commercial products.

The invention claimed is:

1. An absorbent material comprising:
   a blend of a super-absorbent first type of gel-forming fibre with a second type of gel-forming fibre, wherein the super-absorbent first type of gel-forming fibre is formed from a polyacrylate or a co-polymer thereof; and reinforcing fibres.

2. The absorbent material according to claim 1, wherein the second type of gel forming fibre is a polysaccharide.

3. The absorbent material according to claim 1, wherein the second type of gel forming fibre is not modified cellulose.

4. The absorbent material according to claim 2, wherein the second type of gel forming fibre is alginate.

5. The absorbent material according to claim 1, comprising at least 5% of the super-absorbent first type of gel-forming fibres, by weight of the total fibre content of the material.

6. The absorbent material according to claim 1, comprising no more than 50% of the super-absorbent first type of gel-forming fibres, by weight of the total fibre content of the material.

7. The absorbent material according to claim 1, wherein the reinforcing fibres are thermoplastic bicomponent fibres.

8. The absorbent material according to claim 1, wherein the reinforcing fibres are formed from non-modified cellulose.

9. The absorbent material according to claim 1, comprising at least 5% reinforcing fibres, by weight of the total fibre content of the material.

10. The absorbent material according to claim 1, comprising from 10% to 30% of the super-absorbent first type of gel-forming fibres, from 50% to 70% of the second type of gel-forming fibres and from 10% to 20% reinforcing fibres, by weight of the total fibre content of the material.

11. The absorbent material according to claim 10, comprising from 10% to 30% polyacrylate, from 50% to 70% alginate and from 10% to 20% reinforcing fibres, by weight of the total fibre content of the material.

12. An absorbent article cornprising the absorbent material according to claim 1.

13. The absorbent article according to claim 12, wherein the absorbent article is a wound dressing.

14. The absorbent material according to claim 1, wherein the reinforcing fibres are lyocell.

15. The absorbent material according to claim 1, wherein the material is made by a method comprising carding.

16. An absorbent material comprising:
a blend of a super-absorbent first type of gel-forming fibre with a second type of gel-forming fibre, wherein the super-absorbent first type of gel-forming fibre is formed from a poiyacrylate or a co-polymer thereof; and
at least 30% of the second type of gel-forming fibre by weight of the total fibre content of the material.

* * * * *